United States Patent
Davis et al.

[11] Patent Number: 5,091,548
[45] Date of Patent: Feb. 25, 1992

[54] SOLVENTLESS PROCESS FOR PREPARING SULFOPHENETHYLSILOXANE OR SULFONAPHYHYLETHYLSILOXANES

[75] Inventors: P. Davis, Gibraltar, Mich.; J. S. Ku, Baton Rouge, La.; T. M. Schmitt, Dearborn Hgts., Mich.

[73] Assignee: BASF Corporation, Parsippany, N.J.

[21] Appl. No.: 706,913

[22] Filed: May 29, 1991

[51] Int. Cl.$^5$ .............................. C07F 7/08
[52] U.S. Cl. .................................... 556/428
[58] Field of Search .......................... 556/428

[56] References Cited

U.S. PATENT DOCUMENTS

| | | | |
|---|---|---|---|
| 2,789,121 | 4/1957 | Cooper | 556/428 |
| 2,955,128 | 10/1960 | Bailey | 556/428 |
| 4,042,612 | 8/1977 | Magee | 556/428 |
| 4,203,914 | 5/1980 | Finke et al. | 556/428 |
| 4,525,559 | 3/1986 | Paneh et al. | 556/428 |

FOREIGN PATENT DOCUMENTS

| | | | |
|---|---|---|---|
| 247222A1 | 7/1987 | German Democratic Rep. | 556/428 |

Primary Examiner—Paul F. Shaver

[57] ABSTRACT

This invention relates to a process for preparing a sulfophenethylsiloxane having either of the following formulae:

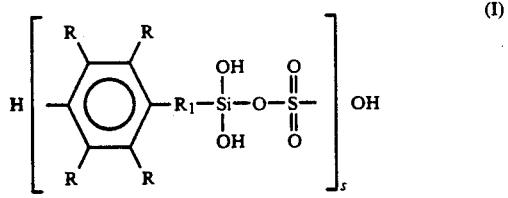

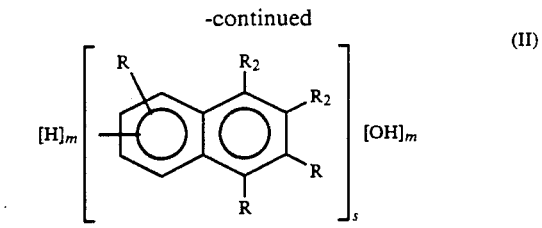

comprising:
(a) adding in essentially equimolar ratio chlorosulfonic acid and a chorosilane having either of the following formulae:

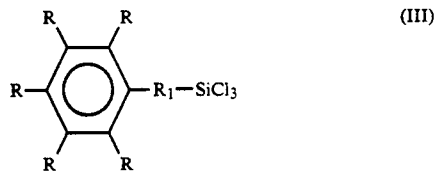

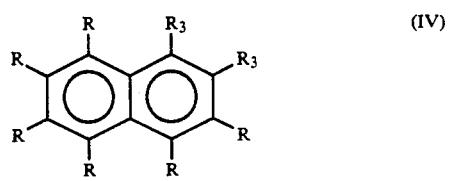

wherein R of formulae I, II, III, and IV is individually hydrogen, halogen, or an alkyl radical having 1 to 4 carbon atoms; $R_1$ is an alkylene radical having 2 to 5 carbon atoms; $R_2$ is R of

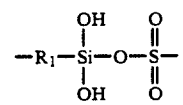

with the proviso that at least one $R_2$ be

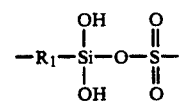

$R_3$ is R or —$R_1SiCl_3$ with the proviso that at least one $R_3$ be —$R_1SiCl_3$ and n is at least 1, m is 1 or 2; continuously through a mixing nozzle in form of small droplets into a continuous stream of air with a temperature of from about 80° C. to about 150° C. in a reaction vessel to form a solid intermediate and
(b) hydrolyzing said intermediate with water.

16 Claims, No Drawings

SOLVENTLESS PROCESS FOR PREPARING SULFOPHENETHYLSILOXANE OR SULFONAPHYHYLETHYLSILOXANES

FIELD OF THE INVENTION

The present invention is directed to a solventless process for production of sulfophenethylsiloxane or sulfonaphthylethylsiloxanes, more specifically it is directed to a solventless process where the reaction of the premixed components takes place in small droplets or in a thin film at elevated temperatures.

BACKGROUND OF THE INVENTION

Sulfophenethylsiloxane or sulfonaphthethylsiloxane and processes for their production are known. The U.S. Pat. No. 2,968,643 describes a reaction of chlorosulfonic acid and a phenyltrichlorosilane to form an intermediate followed by hydrolysis of this intermediate. However, an excess of chlorosulfonic acid is used which has to be separated. The U.S. Pat. No. 4,575,559 discloses a process for the production of sulfophenethylsiloxanes in the presence or absence of solvent. The solventless process in a stirred vessel is technically very difficult because the reaction mixture becomes solid. For this reason most examples use solvents, which must subsequently be removed.

The object of the present invention was to provide a process for the production if sulfophenethylsiloxanes or sulfonaphthylethylsiloxanes which does not use a solvent and which minimizes the formation of by-products.

SUMMARY OF THE INVENTION

The object of the present invention could be achieved with a process for preparing a sulfophenethylsiloxane or sulfonaphthylethylsiloxanes having either of the following formulae:

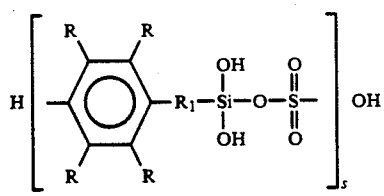

(I)

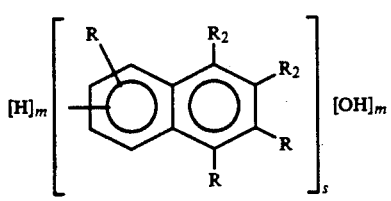

(II)

comprising:
(a) adding in essentially equimolar ratios chlorosulfonic acid and a chlorosilane having either of the following formulae:

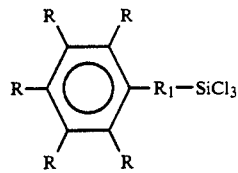

(III)

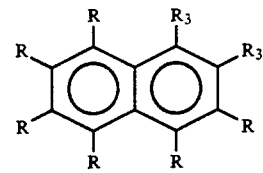

(IV)

wherein R of formulae I, II, III, and IV is individually hydrogen, halogen, or an alkyl radical having 1 to 4 carbon atoms; $R_1$ is an alkylene radical having 2 to 5 carbon atoms; $R_2$ is R or

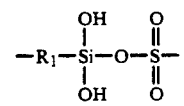

with the proviso that at least one $R_2$ be

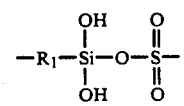

$R_3$ is R or $-R_1SiCl_3$ with the proviso that at least one $R_3$ be $-R_1SiCl_3$ and m and n are each at least 1; continuously through a mixing nozzle in form of small droplets into a continuous stream of air with a temperature of from about 80° C. to about 150° C. in a reaction vessel to form a solid intermediate and
(b) hydrolyzing said intermediate with water.
In an alternative process
(a) the reaction mixture is added as a thin film on the inner surface of a reaction vessel with a temperature of from about 80° C. to about 150° C. to form a solid intermediate and
(b) the said intermediate is hydrolyzed with water.

DETAILED DESCRIPTION OF THE INVENTION

The phenethyltrichlorosilane and naphthylethyltrichlorosilane compounds having structural formula III and IV are well known in the art.

R is hydrogen, halogen or an alkyl radical having 1-4 carbon atoms, $R_1$ is an alkylene radical having 2 to 5 carbon atoms and $R_3$ is R or $-R_1SiCl_3$ with the proviso that at least one $R_3$ be $-R_1SiCl_3$.

Suitable examples of these compounds are β-phenethyltrichlorosilane, α-phenethyltrichlorosilane and naphthylethyltrichlorosilane.

In the process for preparing the sulfophenethylsiloxane or sulfonaphthylethylsiloxane a mixing nozzle is used for mixing the chlorosulfonic acid and the phenethyltrichlorosilane or naphthylethyltrichlorosilane and dispersing the reaction mixture in fine droplets.

A suitable mixing nozzle is formed from two concentric lengths of tubing designed such that mixing and drop formation occur simultaneously. Other configurations may also be used. For example, a glass tee may be used for mixing if the residence time of the mixed material before ejection is short. The concentric configuration is preferred.

The mixing nozzles mix the reactants intensively and disperse the reaction mixture in fine droplets of size from about 0.1 mm to about 5 mm preferably from about 0.5 mm to about 3 mm. These droplets are introduced into a reaction vessel, in which a continuous stream of dry air with a temperature of from about 80° C. to about 150° C., preferably from about 100° to about 120° C., is maintained.

The velocity of the gas stream is not critical in so far as no reactant is carried out of the reaction vessel. In general, the gas stream has a velocity of from about 10 to about 20 feet per second.

The reaction takes place within the small droplets and evolution of hydrogen chloride occurs, which is carried out of the reaction vessel by the gas stream and is collected in a gas trap on the outside of the reaction vessel. The reaction occurs instantly and the reaction product accumulates as a light friable solid on the bottom of the reaction vessel.

The molar ratio of the trichlorosilane compound to chlorosulfonic acid is from about 1.2 to 1.0, preferably from about 1.1 to 1.0.

The reaction is complete when hydrogen chloride can no longer be detected at the exit of the reaction vessel. It is important that the hydrogen chloride evolution is complete because otherwise insoluble by-products are likely to form during the subsequent hydrolysis reaction.

The intermediate is hydrolyzed with water by adding distilled water to the reaction vessel or, preferably, by blowing steam through the reaction vessel. Hydrogen chloride by-product is removed by heating.

The final product is the sulfophenethylsiloxane or sulfonaphthylethylsiloxane which is isolated as a powder from the aqueous solution, or collected from the bottom of the reaction vessel in the case when steam was used.

In an alternative process for preparing sulfophenethylsiloxane or naphthylethylsiloxane, the reaction is carried out in a thin film on the inner surface of a reaction vessel. The chlorosulfonic acid and the trichlorosilane compound are premixed vigorously in a vessel with a stirrer and introduced after homogenization on the inner surface of a reaction vessel, which has a temperature from about 80° C. to about 150° C., preferably from about 100 to about 120° C. The film has a thickness of from about 400 to about 2000 $\mu$m, preferably from about 500 to about 1000 $\mu$m.

The reaction occurs instantly with evolution of hydrogen chloride, which could be carried out of the reaction vessel by a stream of air and which could be collected in a gas trap on the outside of the reaction vessel.

For this reaction also it is important that the hydrogen chloride evolution is complete for the reasons stated above.

The thin film solidifies to the intermediate product, which is hydrolyzed by adding distilled water. The hydrolyzed product is removed by scraping from the surface and evaporating the water and hydrogen chloride by-product.

The yield in both processes is high and is usually of more than 95 percent without significant amounts of environmentally undesirable by-products.

In antifreeze formulations the product is used in amounts of from about 0.02 to about 2.0% by weight in relation to the complete antifreeze formulation.

EXAMPLES

Example 1

Mixing Nozzle

The reaction was accomplished with a 20 mL syringe containing chlorosulfonic acid and a 100 mL syringe containing phenethyltrichlorosilane. The syringe dimensions were such that, if the pistons were advanced the same linear distance, the molar ratio of silane to chlorosulfonic acid delivered was 1.12. The reaction was conducted until the smaller syringe was empty, corresponding to about 35 g chlorosulfonic acid and 81 g silane. The time for addition was about 15 min. Hot air was blown through the chamber to maintain a temperature of 100° C. A scrubber was used to trap escaping hydrochloric acid. The intermediate accumulated as a pile of light, fluffy solid in the bottom of the chamber.

When addition of reagents was complete, 65 g of the solid was worked up by placing on a steam bath overnight, to hydrolyze the chlorinated intermediate to the siloxane. Analysis by infrared and nuclear magnetic resonance spectroscopy, liquid chromatography, and other techniques showed the product to be $\beta$-phenethylsulfosiloxane containing less than 4% soluble and insoluble impurities, thus indicating a yield of 96%.

Example 2

Thin Film

A 1 L pyrex beaker was placed on a hot plate so that the glass had an estimated temperature of 100° C. 600 L trichlorophenethylsilane and 200 L chlorosulfonic acid were added to a vial, mixed and immediately poured onto the bottom of the beaker. After 1 min., 3 mL water was added, and the mixture was evaporated to dryness. When cool, the layer was removed by scraping with a rubber policeman and slurrying with 1 mL water. The water was evaporated to give the powdery residue. Analysis by infrared spectroscopy showed the product to be $\beta$-phenethylsulfosiloxane, with no impurities evident.

We claim:

1. A process for preparing a sulfophenethylsiloxane having either of the following formulae:

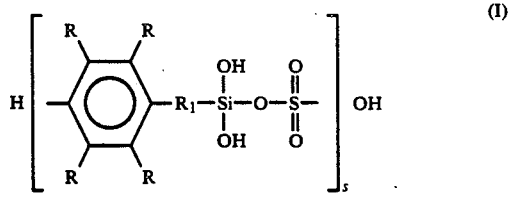

(I)

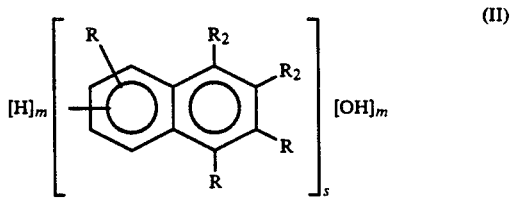

(II)

comprising:

(a) adding in essentially equimolar ratio chlorosulfonic acid and a chlorosilane having either of the following formulae:

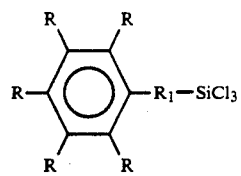

(III)

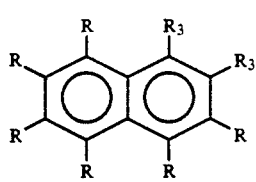

(IV)

wherein R of formulae I, II, III, and IV is individually hydrogen, halogen, or an alkyl radical having 1 to 4 carbon atoms; $R_1$ is an alkylene radical having 2 to 5 carbon atoms; $R_2$ is R or

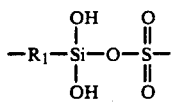

with the proviso that at least one $R_2$ be

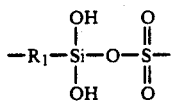

$R_3$ is R or $-R_1SiCl_3$ with the proviso that at least one $R_3$ be $-R_1SiCl_3$ and m and n are each at least 1 continuously through a mixing nozzle in form of small droplets into a continuous stream of air with a temperature of from about 80° C. to about 150° C. in a reaction vessel to form a solid intermediate and (b) hydrolyzing said intermediate with water.

2. The process according to claim 1, wherein said droplets have a size of about 0.1 mm to about 5 mm.

3. The process according to claim 1, wherein said continuous stream of air has a temperature of from about 90° C. to 120° C.

4. The process according to claim 1, wherein n is 2 to 4.

5. The process according to claim 1, wherein the intermediate is heated to a temperature from about 60 to about 95° C. during hydrolysis.

6. The process according to claim 1, wherein the intermediate is cooled prior to hydrolysis.

7. The process according to claim 1, wherein the phenethyltrichlorosilane is β-phenethyltrichlorosilane.

8. The process according to claim 1, wherein the molar ratio of β-phenethyltrichlorosilane to chlorosulfonic acid is from about 1.2 to 1.0

9. A process for preparing a sulfophenethylsiloxane having either of the following formulae:

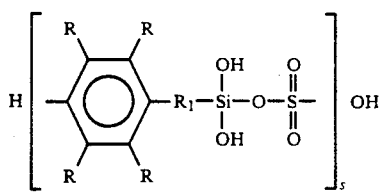

(I)

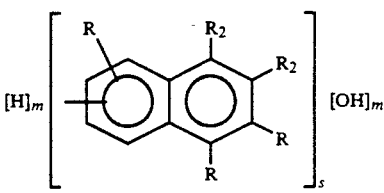

(II)

comprising:
(a) mixing in essentially equimolar ratio chlorosulfonic acid and a chlorosilane having either of the following formulae:

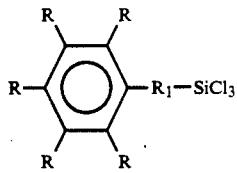

(III)

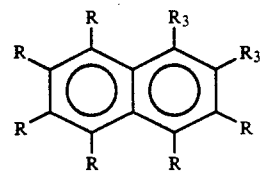

(IV)

wherein R of formulae I, II, III, and IV is individually hydrogen, halogen, or an alkyl radical having 1 to 4 carbon atoms; $R_1$ is an alkylene radical having 2 to 5 carbon atoms; $R_2$ is R or

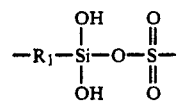

with the proviso that at least one $R_2$ be

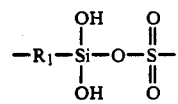

$R_3$ is R or $-R_1SiCl_3$ with the proviso that at least one $R_3$ be $-R_1SiCl_3$; and m and n are each at least 1 adding the mixture as a thin film on the inner surface of a reaction vessel with a temperature of from about 80° C. to about 150° C. to form a solid intermediate and (b) hydrolyzing said intermediate with water.

10. The process according to claim 9, wherein said film has a thickness of from about 400 to about 200 μm.

11. The process according to claim 9, wherein said inner surface has a temperature of from about 90° C. to about 120° C.

12. The process according to claim 9, wherein n is 2 to 4.

13. The process according to claim 9, wherein the intermediate is heated to a temperature from about 60 to about 95° C. during hydrolysis.

14. The process according to claim 9, wherein the intermediate is cooled prior to hydrolysis.

15. The process according to claim 9, wherein the phenethyltrichlorosilane is β-phenethyltrichlorosilane.

16. The process according to claim 9, wherein the molar ratio of β-phenethyltrichlorosilane to chlorosulfonic acid is from about 1.2 to 1.0.

* * * * *